US008882687B2

(12) United States Patent
Hannnigan et al.

(10) Patent No.: US 8,882,687 B2
(45) Date of Patent: *Nov. 11, 2014

(54) NEGATIVE PRESSURE TREATMENT SYSTEM WITH HEATING AND COOLING PROVISION

(71) Applicant: KCI Licensing, Inc., San Antonio, TX (US)

(72) Inventors: Raymond R. Hannnigan, San Antonio, TX (US); James R. Leininger, San Antonio, TX (US); Charles I. Biltz, San Antonio, TX (US); Frank Dilazzaro, San Antonio, TX (US); Christopher Fashek, San Antonio, TX (US); Royce W. Johnson, Universal City, TX (US); Wayne J. Schroeder, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 10 days.

This patent is subject to a terminal disclaimer.

(21) Appl. No.: 13/756,313

(22) Filed: Jan. 31, 2013

(65) Prior Publication Data

US 2013/0204211 A1 Aug. 8, 2013

Related U.S. Application Data

(60) Continuation of application No. 12/475,002, filed on May 29, 2009, now Pat. No. 8,372,022, which is a (Continued)

(51) Int. Cl.
*A61F 5/00* (2006.01)
*A61M 35/00* (2006.01)

(Continued)

(52) U.S. Cl.
CPC ............ *A61F 7/0085* (2013.01); *A61M 1/0088* (2013.01); *A61M 2205/366* (2013.01); *A61F*

(Continued)

(58) Field of Classification Search
CPC ........... A61F 7/007; A61F 7/02; A61F 13/00; A61F 13/02; A61F 13/023; A61F 13/0203; A61M 1/0088; A61M 35/00; A61L 2300/404
USPC ............... 602/2; 604/289–292, 304–308, 313
See application file for complete search history.

(56) References Cited

U.S. PATENT DOCUMENTS 1,355,846 A 10/1920 Rannells
2,547,758 A 4/1951 Keeling (Continued)

FOREIGN PATENT DOCUMENTS

AU 550575 A1 3/1986
AU 745271 4/1999

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Kim M Lewis

(57) ABSTRACT

A method, and apparatus for the controlled acceleration, and/ or retardation of the body's inflammatory response generally comprises a foam pad for insertion substantially into a wound site, a heating, a cooling pad for application over the wound site, a wound drape or sealing enclosure of the foam pad, the heating, and cooling pad at wound site. The foam pad is placed in fluid communication with a vacuum source for promotion of the controlled acceleration or retardation of the body's inflammatory response. The heating, and cooling provision controls the local metabolic function as part of the inflammatory response.

50 Claims, 1 Drawing Sheet

Related U.S. Application Data division of application No. 11/545,142, filed on Oct. 10, 2006, now Pat. No. 7,540,848, which is a continuation of application No. 09/937,937, filed as application No. PCT/US00/08759 on Mar. 31, 2000, now Pat. No. 7,144,390.

(60) Provisional application No. 60/127,596, filed on Apr. 2, 1999.

(51) Int. Cl.
*A61M 1/00* (2006.01)
*A61F 7/10* (2006.01)
*A61F 13/00* (2006.01)
*A61F 7/00* (2006.01)
*A61F 13/06* (2006.01)

(52) U.S. Cl.
CPC .. 7/10 (2013.01); *A61F 2013/00174* (2013.01); *A61F 2013/0054* (2013.01); *A61F 13/00068* (2013.01); *A61F 2013/00519* (2013.01); *A61F 2007/0063* (2013.01); *A61M 2205/3606* (2013.01); *A61F 2013/00412* (2013.01); *A61F 2013/00157* (2013.01); *A61F 2013/00536* (2013.01); *A61F 2013/0074* (2013.01); *A61F 2007/0056* (2013.01); *A61F 13/069* (2013.01)
USPC .............. 602/2; 604/290; 604/291; 604/304; 604/305; 604/303

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,144,390 B1 * | 12/2006 | Hannigan et al. .............. 604/313 |
| 7,540,848 B2 * | 6/2009 | Hannigan et al. .................. 602/2 |
| 8,372,022 B2 * | 2/2013 | Hannigan et al. .................. 602/2 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |

(56) References Cited

FOREIGN PATENT DOCUMENTS

| | | |
|---|---|---|
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain—Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

NEGATIVE PRESSURE TREATMENT SYSTEM WITH HEATING AND COOLING PROVISION

CROSS-REFERENCE TO RELATED APPLICATIONS

This application is a continuation of U.S. patent application Ser. No. 12/475,002 filed May 29, 2009, now U.S. Pat. No. 8,372,022 which is a divisional of U.S. patent application Ser. No. 11/545,142, filed Oct. 10, 2006, now U.S. Pat. No. 7,540,848 issued Jun. 2, 2009 which is a continuation of U.S. patent application Ser. No. 09/937,937, filed Oct. 2, 2001, now U.S. Pat. No. 7,144,390 issued Dec. 5, 2006, which is a national stage application of International Application No. PCT/US00/08759, filed Mar. 31, 2000, which claims the benefit of U.S. Provisional Application No. 60/127,596, filed Apr. 2, 1999. All of the above-referenced applications are hereby incorporated by reference.

BACKGROUND OF THE INVENTION

1. Field of the Invention

The present invention relates to the healing of wounds. More specifically, the present invention relates to the vacuum assisted closure of wounds wherein localized heating or cooling is used to accelerate or retard the metabolic function of the inflammatory system in order to facilitate wound healing.

2. Description of Related Art

Wound closure involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and thus are less able to naturally close the wound. Until recently, such difficult wounds were addressed only through the use of sutures or staples.

Although still widely practiced and often effective, such mechanical closure techniques suffer a major disadvantage in that they produce tension on the skin tissue adjacent the wound. In particular, the tensile force required in order to achieve closure using sutures or staples causes very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative pressure, commonly referred to as vacuum assisted closure (VAC) therapy, typically involves mechanical-like contraction of the wound with simultaneous removal of excess fluid. In this manner, applying negative pressure augments the body's natural inflammatory process while alleviating many of the known intrinsic side effects, such as the production of edema caused by increased blood flow absent the necessary vascular structure for proper venous return.

While applying negative pressure has been highly successful in the promotion of wound closure, healing many wounds previously thought largely untreatable, some difficulty remains. Because the inflammatory process is very unique to the individual patient, even the addition of negative pressure does not result in a fast enough response for closure of some wounds, especially when applied during the occlusion and initial cleanup and rebuilding stages. It is therefore a principle object of the present invention to provide a method and apparatus whereby the known negative pressure modalities are improved through controlled acceleration of the inflammatory response.

Additionally, and again at least partially attributable to the variance between patients, it is possible that a properly initiated inflammatory response may be taken too far, resulting in edema and pain. It is therefore another principle object of the present invention to provide a method and apparatus whereby the known negative pressure modalities are improved through controlled retardation of the inflammatory response.

SUMMARY

In accordance with the foregoing objects, the present invention—a method and apparatus for the controlled acceleration and/or retardation of the body's inflammatory response—generally comprises a foam pad for insertion substantially into a wound site, a heating and cooling pad for application over the wound site and a wound drape for sealing enclosure of the foam pad and the heating and cooling pad at the wound site. According to the invention, the foam pad is placed in fluid communication with a vacuum source for promotion of fluid drainage while warm or cool fluid is circulated through the heating and cooling pad for the controlled acceleration or retardation, respectively, of the metabolic function portion of the body's inflammatory response.

According to the preferred embodiment of the present invention, a heating and cooling provision is added to the previously known application of negative pressure to control the local metabolic function as part of the inflammatory response. By providing localized heating in combination with the otherwise ordinary application of negative pressure, the overall inflammatory response can be synergistically accelerated to produce rapid capillary occlusion and earlier initiation of the cleanup and rebuilding stages. Likewise, in the event that the attending clinician determines that the inflammatory response has been over-activated, localized cooling may be provided in combination with the application of negative pressure to retard the body's inflammatory response without sacrifice of the edema control and other aspects of the otherwise provided negative pressure.

In the preferred embodiment of the present invention, the heating and cooling pad comprises a flexible and breathable water layer, generally comprising two sheets of RF-weldable material. The two sheets of the pad are RF-welded together in a waffle-like pattern, wherein a plurality of apertures is formed between a plurality of channels. The apertures allow the transpiration of moisture from the patient's skin while the channels allow the circulation, via a supply tube and a drainage tube, of warm or cool water, as required, through the pad for the heating or cooling thereof.

While the heating and cooling pad may be placed inside or outside of the wound drape during the heating aspect of the present invention, it is critical that the heating and cooling pad be placed inside of the wound drape during the cooling aspect of the present invention. In this manner, condensate formation on the interior of the drape, which may cause the drape's adhesive to loosen and ultimately result in loss of vacuum at the wound site, can be minimized. In particular, placing the heating and cooling pad inside the wound drape limits the surrounding moisture content to that existing and generated within the confines of the wound site, which is minimized by the suction aspect of the negative pressure.

Because the cooling aspect of the present invention should be implemented in this manner and the clinician may indicate the need for cooling at any time after initiation of the application of negative pressure, the preferred method of the present invention comprises placing the heating and cooling pad beneath the wound drape, adjacent the foam pad and wound site, regardless of whether heating or cooling is initially indicated. Upon placement of the pad, the wound drape is firmly adhered about the supply tube and drainage tube to prevent vacuum leakage.

Finally, many other features, objects and advantages of the present invention will be apparent to those of ordinary skill in relevant arts, especially in light of the foregoing discussions, the following drawings and exemplary detailed description and the claims appended hereto.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF ILLUSTRATIVE EMBODIMENTS

Figure 1:
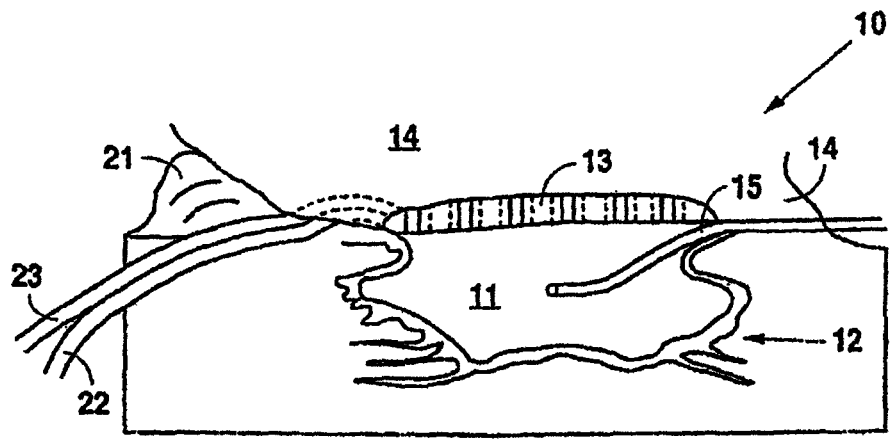
FIG. 1 shows, in partially cut away perspective view, the preferred embodiment of the present invention as applied to a mammalian wound site.
Figure 2:
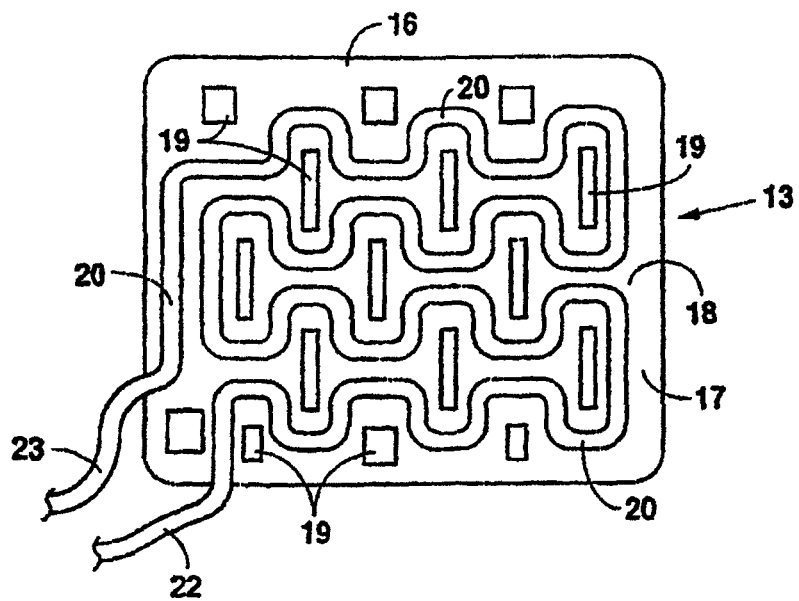
FIG. 2 shows, in top cross-sectional plan view, the heating and cooling pad of the invention of FIG. 1.

Although those of ordinary skill in the art will readily recognize many alternative embodiments, especially in light of the illustrations provided herein, this detailed description is exemplary of the preferred embodiment of the present invention—a vacuum assisted closure system with heating and cooling provision, the scope of which is limited only by the claims appended hereto.

Referring now to the figures, the present invention 10 is shown to, generally comprise a foam pad 11 for insertion substantially into a wound site 12, a heating and cooling pad 13 for application over the wound site 12 and a wound drape 14 for sealing enclosure of the foam pad 11 and the heating and cooling pad 13 at the wound site 12. According to the invention, the foam pad 11 is placed in fluid communication with a vacuum source for promotion of fluid drainage while warm or cool fluid is circulated through the heating and cooling pad 13 for the controlled acceleration or retardation, respectively, of the metabolic function portion of the body's inflammatory response.

According to the preferred embodiment of the present invention, the foam pad 11, wound drape 14 and vacuum source are implemented as known in the prior art, each of which is detailed in U.S. patent application Ser. No. 08/517,901 filed Aug. 22, 1995. By this reference, the full disclosure of U.S. patent application Ser. No. 08/517,901 ("the '901 application"), including the claims and the drawings, is incorporated herein as though now set forth in its entirety. Additionally, such a negative pressure system is readily commercially available through Kinetic Concepts, Inc. of San Antonio, Tex., U.S.A. and/or its subsidiary companies.

As detailed in the '901 application, the foam pad 11 preferably comprises a highly reticulated, open-cell polyurethane or polyether foam for good permeability of wound fluids while under suction. As also detailed in the '901 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '901 application also details the wound drape 14, which preferably comprises an elastomeric material at least peripherally covered with a pressure sensitive, acrylic adhesive for sealing application over the wound site 12.

According to the preferred method of the present invention, those components as are described in the '901 application are generally employed as known in the art with the exception that the heating and cooling provision of the present invention is added to control the local metabolic function as part of the inflammatory response. By providing localized heating in combination with the otherwise ordinary application of negative pressure, the overall inflammatory response can be synergistically accelerated to produce rapid capillary occlusion and earlier initiation of the cleanup and rebuilding stages. Likewise, in the event that the attending clinician determines that the inflammatory response has been over-activated, localized cooling may be provided in combination with the application of negative pressure to retard the body's inflammatory response without sacrifice of the edema control and other aspects of the otherwise provided negative pressure.

In the preferred embodiment of the present invention, the heating and cooling pad 13 comprises a flexible and breathable water layer 16, generally comprising two sheets 17 (one not shown) of RF-weldable material. The two sheets 17 of the pad are RF-welded together in a waffle-like pattern, wherein a plurality of apertures 19 is formed between a plurality of channels 20. The apertures 19 allow the transpiration of moisture from the patient's skin 21 while the channels 20 allow the circulation, via a supply tube 22 and a drainage tube 23, of warm or cool water, as required, through the pad 13 for the heating or cooling thereof.

While the heating and cooling pad 13 may be placed inside or outside of the wound drape 14 during the heating aspect of the present invention, it is critical that the heating and cooling pad 13 be placed inside of the wound drape 14 during the cooling aspect of the present invention. In this manner, condensate formation on the interior and near the edges of the drape 14, which may cause the drape's adhesive to loosen and ultimately result in loss of vacuum at the wound site 12, can be minimized. In particular, placing the heating and cooling pad 13 inside the wound drape 14 limits the surrounding moisture content to that moisture level existing and generated within the confines of the wound site 12, which is minimized by the suction aspect of the negative pressure.

Because the cooling aspect of the present invention should be implemented in this manner and the clinician may indicate the need for cooling at any time after initiation of the application of negative pressure, the preferred method of the present invention comprises placing the heating and cooling pad 13 beneath the wound drape 14, adjacent the foam pad 11 and wound site 12, regardless of whether heating or cooling is initially indicated. Upon placement of the pad 13, the wound drape 14 is firmly adhered about the supply tube 22 and the drainage tube 23 to prevent vacuum leakage.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and the claims drawn hereto. For example, those of ordinary skill in the art will recognize that the heating and cooling pad 13 may be constructed in a wide variety of shapes, sizes and internal structures. Such an alternative embodiment may comprise the integration of the heating and cooling pad 13 into a multi-layered version of the wound drape 14. In any case, because the scope of the present invention is much broader than any particular embodiment, the foregoing detailed description should not be construed as a limitation of the present invention, which is limited only by the claims appended hereto.

We claim:

1. An apparatus for controlling blood flow through damaged tissue, comprising:
    a porous pad configured to be placed proximate the damage tissue and adapted to be fluidly coupled to a source of negative pressure for providing a vacuum proximate the damaged tissue;
    a drape having an adhesive adapted to form an enclosure for sealing the porous pad to maintain a vacuum proximate the damaged tissue; and
    a thermal control element configured to be placed proximate the damaged tissue, the thermal control element having a pair of flexible sheets connected to form at least one fluid channel between the sheets to receive a circulated fluid, the thermal control element further including at least one aperture passing through the sheets to allow transpiration of moisture through the sheets.

2. The apparatus according to claim 1, wherein the at least one fluid channel receives the circulated fluid at a temperature greater than the temperature proximate the damaged tissue.

3. The apparatus according to claim 2, wherein the circulated fluid is water.

4. The apparatus according to claim 1, wherein the at least one fluid channel receives the circulated fluid at a temperature less than the temperature proximate the damaged tissue.

5. The apparatus according to claim 4, wherein the circulated fluid is water.

6. The apparatus according to claim 1, wherein the thermal control element is placed in contact with the porous pad beneath the drape.

7. The apparatus according to claim 1, wherein the thermal control element is placed in contact with the porous pad beneath the drape, and the at least one fluid channel receives the circulated fluid at a temperature greater than the temperature proximate the damaged tissue.

8. The apparatus according to claim 1, wherein the thermal control element is placed in contact with the porous pad beneath the drape, and the at least one fluid channel receives the circulated fluid at a temperature less than the temperature proximate the damaged tissue.

9. The apparatus according to claim 1, wherein the drape is disposed between the thermal control element and the porous pad.

10. The apparatus according to claim 1, wherein the drape is disposed between the thermal control element and the porous pad, and the at least one fluid channel receives the circulated fluid at a temperature greater than the temperature proximate the damaged tissue.

11. The apparatus according to claim 1, wherein the pair of sheets is connected by RF welds.

12. An apparatus for controlling blood flow through damaged tissue, comprising:
    a porous pad configured to be placed proximate the damaged tissue and adapted to be fluidly coupled to a source of negative pressure for providing a vacuum proximate the damaged tissue;
    a drape adapted to form an enclosure for sealing the porous pad to maintain a vacuum proximate the damaged tissue; and
    a heating element placed proximate the damaged tissue and having a breathable water layer having fluid channels and apertures between the fluid channels.

13. The apparatus according to claim 12, wherein the heating element is placed in contact with the porous pad.

14. The apparatus according to claim 12, wherein the drape has an adhesive for sealing the porous pad proximate the damaged tissue.

15. The apparatus according to claim 12, wherein the drape is disposed between the heating element and the porous pad.

16. The apparatus according to claim 12, wherein the breathable water layer further comprises a first sheet connected to a second sheet to form the fluid channels.

17. The apparatus according to claim 16, wherein the first and second sheets are flexible.

18. The apparatus according to claim 12, wherein the fluid channels are continuous.

19. The apparatus according to claim 12, wherein the fluid channels include an inlet configured for connection to a supply tube and an outlet configured for connection to a drainage tube.

20. The apparatus according to claim 12, wherein the breathable water layer further comprises a first sheet connected to a second sheet to form the fluid channels, and wherein the fluid channels are continuous and include an inlet configured for connection to a supply tube and an outlet configured for connection to a drainage tube.

21. The apparatus according to claim 12, wherein the fluid channels receive a circulating fluid at a temperature greater than the temperature proximate the damaged tissue.

22. The apparatus according to claim 12, wherein the heating element further comprises a cooling element.

23. The apparatus according to claim 12, wherein the heating element further comprises a cooling element, and the fluid channels receive a circulating fluid at a temperature less than the temperature proximate the damaged tissue.

24. An apparatus for controlling blood flow through damaged tissue, comprising:
    a porous pad configured to be placed proximate the damaged tissue and adapted to be fluidly coupled to a source of negative pressure for providing a vacuum proximate the damaged tissue;

a drape adapted to form an enclosure for sealing the porous pad to maintain a vacuum proximate the damaged tissue; and a cooling element in contact with the porous pad and having a breathable water layer having fluid channels and apertures between the fluid channels.

25. The apparatus according to claim 24, wherein in the drape has an adhesive for sealing the porous pad proximate the damaged tissue.

26. The apparatus according to claim 24, wherein the breathable water layer further comprises a first sheet connected to a second sheet to form the fluid channels.

27. The apparatus according to claim 24, wherein the fluid channels are continuous.

28. The apparatus according to claim 24, wherein the fluid channels include an inlet configured for connection to a supply tube and an outlet configured for connection to a drainage tube.

29. The apparatus according to claim 24, wherein the breathable water layer further comprises a first sheet connected to a second sheet to form the fluid channels, and wherein the fluid channels are continuous and include an inlet configured for connection to a supply tube and an outlet configured for connection to a drainage tube.

30. The apparatus according to claim 24, wherein the fluid channels receive a circulating fluid at a temperature less than the temperature proximate the damaged tissue.

31. A method for controlling blood flow through damaged tissue, comprising:
securing a porous pad and a breathable layer in a sealed environment proximate the damaged tissue;
maintaining a vacuum in the sealed environment;
circulating a fluid through fluid channels in the breathable layer while transporting moisture away from the sealed environment through apertures in the breathable layer; and
regulating the temperature proximate the damaged tissue with the circulated fluid.

32. The method according to claim 31, further comprising alternating the temperature of the fluid between temperatures greater than the temperature proximate the damaged tissue and temperatures less than the temperature proximate the damaged tissue.

33. The method according to claim 31, further comprising providing the fluid at a temperature greater than the temperature proximate the damaged tissue.

34. The method according to claim 31 further comprising providing the fluid at a temperature less than the temperature proximate the damaged tissue.

35. The method according to claim 31 further comprising distributing vacuum within the sealed environment through the porous pad.

36. The method according to claim 31, wherein the fluid is water.

37. The method according to claim 31, further comprising:
alternating the temperature of the fluid between temperatures greater than the temperature proximate the damaged tissue and temperatures less than the temperature proximate the damaged tissue; and
distributing vacuum within the sealed environment through the porous pad.

38. The method according to claim 31, further comprising: placing the breathable layer in contact with the porous pad.

39. The method according to claim 31, further comprising:
placing the breathable layer in contact with the porous pad; and
covering the breathable layer and the porous pad with a drape to form the sealed environment.

40. The method according to claim 31, further comprising:
covering the porous pad with a drape to form the sealed environment; and
placing the breathable layer over the drape such that the drape is disposed between the porous pad and the breathable layer.

41. The method according to claim 40, wherein the drape has an adhesive.

42. The method according to claim 41, further comprising:
applying vacuum proximate the damaged tissue though the apertures.

43. The method according to claim 41, wherein the breathable layer has a pair of flexible sheets connected to form the fluid channels between the sheets to receive the fluid, the pair of flexible sheets further including the apertures.

44. The method according to claim 41, wherein the pair of flexible sheets is connected by RF welds.

45. The method according to claim 41, wherein the fluid channels are continuous.

46. The method according to claim 41, wherein the fluid channels include an inlet configured for connection to a supply tube and an outlet configured for connection to a drainage tube.

47. The method according to claim 41 further comprising:
regulating the temperature proximate the damaged tissue with the circulated fluid based on an inflammatory response of the damaged tissue.

48. A method for controlling blood flow through damaged tissue, comprising:
placing a porous pad proximate the damaged tissue;
placing a thermal control element in contact with the porous pad;
covering the thermal control element and the porous pad with a drape;
applying a vacuum to the porous pad;
circulating a fluid through fluid channels in the thermal control element; and
allowing moisture transpiration proximate the damaged tissue through apertures in the thermal control element.

49. The method according to claim 48, further comprising:
regulating the temperature proximate the damaged tissue with the circulated fluid.

50. The method according to claim 48, wherein the thermal control element is at least one of a heating element and a cooling element.

* * * * *

UNITED STATES PATENT AND TRADEMARK OFFICE
CERTIFICATE OF CORRECTION

PATENT NO. : 8,882,687 B2
APPLICATION NO. : 13/756313
DATED : November 11, 2014
INVENTOR(S) : Raymond R. Hannigan et al.

Page 1 of 1

It is certified that error appears in the above-identified patent and that said Letters Patent is hereby corrected as shown below:

On the Title Page, Item (12) and (75)

In the inventors, correct the spelling of Hannnigan to Hannigan

Signed and Sealed this
Fourth Day of August, 2015

Michelle K. Lee
*Director of the United States Patent and Trademark Office*